United States Patent
den Braber

(10) Patent No.: US 9,332,724 B2
(45) Date of Patent: May 10, 2016

(54) SPINACH LINE SP6111

(75) Inventor: Jan Hugo den Braber, Klundert (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 52 days.

(21) Appl. No.: 13/267,340

(22) Filed: Oct. 6, 2011

(65) Prior Publication Data

US 2012/0107458 A1    May 3, 2012

Related U.S. Application Data

(60) Provisional application No. 61/407,215, filed on Oct. 27, 2010.

(51) Int. Cl.
*A01H 1/00* (2006.01)
*C07H 21/04* (2006.01)
*C07K 14/415* (2006.01)
*C12N 15/00* (2006.01)
*A01H 5/12* (2006.01)
*C12Q 1/68* (2006.01)
*A23L 1/212* (2006.01)

(52) U.S. Cl.
CPC .............. *A01H 5/12* (2013.01); *A23L 1/2123* (2013.01); *C12Q 1/6895* (2013.01); *C12Q 2600/156* (2013.01)

(58) Field of Classification Search
CPC .. A01H 5/12; C12Q 1/6895; C12Q 2600/156; A23L 1/2123
USPC ......................................................... 800/295
See application file for complete search history.

(56) References Cited

U.S. PATENT DOCUMENTS 7,935,864 B2 * 5/2011 Baerends ...................... 800/295

* cited by examiner

*Primary Examiner* — Li Zheng
(74) *Attorney, Agent, or Firm* — Vedder Price P.C.; Thomas J. Kowalski; Deborah L. Lu

(57) ABSTRACT

Spinach, parts thereof, and the making and use thereof, including with respect to the inbred spinach line called SP6111 are disclosed.

29 Claims, 1 Drawing Sheet

SPINACH LINE SP6111

INCORPORATION BY REFERENCE

This application claims the benefit of U.S. Provisional No. 62/407,215 filed Oct. 27, 2010. All documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference

FIELD OF THE INVENTION

The present invention relates to the field of plant breeding and more particular to the development of inbred spinach line SP6111.

BACKGROUND OF THE INVENTION

Spinach (*Spinacia oleracea*) is a flowering vegetable plant in the family of Amaranthaceae. It is native to southwestern and central Asia, but nowadays is being cultivated worldwide, mostly in temperate regions. The consumable parts of spinach are the leaves. These are produced during the first stage of the life cycle of a spinach plant, during which the plant forms a leaf rosette. The second stage is the flowering stage or bolting stage. Bolting is the growth of an elongated stalk with flowers grown from within the main stem of a plant. During the bolting stage it is not possible anymore to harvest any marketable product of the plant.

The leaves of a spinach plant are usually sold loose, bunched, in prepackaged bags, canned, or frozen. There are three basic types of spinach, namely savoy, semi-savoy and smooth. Savoy has dark green, crinkly and curly leaves. Flat or smooth leaf spinach has broad smooth leaves. Semi-savoy is a hybrid variety with slightly crinkled leaves.

SUMMARY OF THE INVENTION

The present invention provides a new inbred line of spinach plants, called SP6111. Seeds of inbred spinach line SP6111 have been deposited with the National Collections of Industrial, Marine and Food Bacteria (NCIMB) in Bucksburn, Aberdeen AB21 9YA, Scotland, UK and have been assigned NCIMB Accession No. 41758.

In one embodiment, the invention provides a spinach plant resistant against downy mildew (*Peronospora farinose* f.sp. *spinaciae* (Pfs)) isolate US2209, representative seed of which having been deposited under NCIMB Accession No. 41758.

In one embodiment, the invention provides a spinach plant resistant against downy mildew (*Peronospora farinose* f.sp. *spinaciae* (Pfs)) races 1, 3, 5, 8, 9, and 11, representative seed of which having been deposited under NCIMB Accession No. 41758.

In one embodiment, the invention provides a spinach plant resistant against downy mildew (*Peronospora farinose* f.sp. *spinaciae* (Pfs)) races 1, 3, 5, 8, 9, 11, and downy mildew isolate US2209, representative seed of which having been deposited under NCIMB Accession No. 41758.

In one embodiment, the invention provides a spinach plant exhibiting a combination of traits including medium bolting, fast growing, dark green leaf color at maturity, a round leaf tip, arrow shaped leafs, and resistance to downy mildew (*Peronospora farinose* f.sp. *spinaciae* (Pfs)) isolate US2209, representative seed of which having been deposited under NCIMB Accession No. 41758. (The growth rate of the spinach plant of the invention, e.g. SP6111, representative seed of which having been deposited under NCIMB Accession No. 41758, is comparable to dixie market (see e.g. US2009/0300787). The bolting of the spinach plant of the invention, e.g. SP6111, representative seed of which having been deposited under NCIMB Accession No. 41758, is comparable to Bloomsdale (e.g. US20100031381). And the color of the spinach plant of the invention, e.g. SP6111, representative seed of which having been deposited under NCIMB Accession No. 41758, is akin to Bloomsdale, see also table 2.)

In one embodiment, the invention provides a spinach plant exhibiting a combination of traits including medium bolting, fast growing, dark green leaf color at maturity, a round leaf tip, arrow shaped leafs, and resistance to downy mildew (*Peronospora farinose* f.sp. *spinaciae* (Pfs)) races 1, 3, 5, 8, 9, 11, representative seed of which having been deposited under NCIMB Accession No. 41758.

In one embodiment, the invention provides a spinach plant exhibiting a combination of traits including medium bolting, fast growing, dark green leaf color at maturity, a round leaf tip, arrow shaped leafs, and resistance to downy mildew (*Peronospora farinose* f.sp. *spinaciae* (Pfs)) races 1, 3, 5, 8, 9, 11, and downy mildew isolate US2209, representative seed of which having been deposited under NCIMB Accession No. 41758.

In one embodiment, the invention provides a spinach plant designated SP6111, representative seed of which having been deposited under NCIMB Accession No. 41758.

In an embodiment of the present invention, there also is provided parts of a spinach plant of the invention, including parts of a spinach plant having resistance against downy mildew (*Peronospora farinose* f.sp. *spinaciae* (Pfs)) isolate US2209, or parts of a spinach plant having resistance to downy mildew (*Peronospora farinose* f.sp. *spinaciae* (Pfs)) races 1, 3, 5, 8, 9, 11, or parts of a spinach plant having resistance to both downy mildew (*Peronospora farinose* f.sp. *spinaciae* (Pfs)) isolate US2209, and downy mildew (*Peronospora farinose* f.sp. *spinaciae* (Pfs)) races 1, 3, 5, 8, 9, 11, or parts of a spinach plant having any of the aforementioned resistance(s) and a combination of traits including medium bolting, fast growing, dark green leaf color at maturity, a round leaf tip, arrow shaped leafs, or parts of a spinach plant having any of the aforementioned resistance(s) and one or more morphological or physiological characteristics tabulated herein, including parts of inbred spinach line SP6111, wherein the plant parts are suitable for sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts can come from include those wherein representative seed of which has been deposited under NCIMB Accession No.

NCIMB 41758. With regard to morphological or physiological characteristics, it is understood that these are compared when plants are grown in the same environmental conditions.

In another embodiment there is a plant grown from seeds, representative seed of which having been deposited under NCIMB Accession No. 41758. In a further embodiment there is a plant regenerated from the above-described plant parts or regenerated from the above-described tissue culture. Advantageously such a plant has morphological and/or physiological characteristics of inbred spinach line SP6111 and/or of plant grown from seed, representative seed of which having been deposited under NCIMB Accession No. NCIMB 41758—including without limitation such plants having all of the morphological and physiological characteristics of inbred spinach line SP6111 and/or of plant grown from seed, representative seed of which having been deposited under NCIMB Accession No. NCIMB 41758. Accordingly, in still a further embodiment, there is provided a spinach plant having all of the morphological and physiological characteristics of inbred spinach line SP6111, representative seed of which having been deposited under NCIMB Accession No. NCIMB 41758. Such a plant can be grown from the seeds, regenerated from the above-described plant parts, or regenerated from the above-described tissue culture. A spinach plant having any of the aforementioned resistance(s), a spinach plant having any of the aforementioned resistance(s) and one or more morphological or physiological characteristics recited or tabulated herein, and a spinach plant advantageously having all of the aforementioned resistances and the characteristics recited and tabulated herein, are preferred. Parts of such plants—such as those plant parts above-mentioned—are encompassed by the invention.

In one embodiment, there is provided progeny of inbred spinach line SP6111 produced by sexual or vegetative reproduction, grown from seeds, regenerated from the above-described plant parts, or regenerated from the above-described tissue culture of the inbred spinach line or a progeny plant thereof, representative seed of which having been deposited under NCIMB Accession No. NCIMB 41758.

In another embodiment, there is provided progeny of inbred spinach line SP6111 produced by sexual or vegetative reproduction, grown from seeds, regenerated from the above-described plant parts, or regenerated from the above-described tissue culture of the inbred spinach line or a progeny plant thereof, in which the regenerated plant is resistant against downy mildew (*Peronospora farinose* f.sp. *spinaciae* (Pfs)) isolate US2209, representative seed of which having been deposited under NCIMB Accession No. NCIMB 41758.

Progeny of the inbred spinach line SP6111 can be modified in one or more other characteristics, in which the modification is a result of, for example and without limitation, mutagenesis or transformation with a transgene.

In still another embodiment, there is provided progeny of inbred spinach line SP6111 produced by sexual or vegetative reproduction, grown from seeds, regenerated from the above-described plant parts, or regenerated from the above-described tissue culture of the inbred spinach line or a progeny plant thereof, in which the regenerated plant is resistant against downy mildew (*Peronospora farinose* f.sp. *spinaciae* (Pfs)) isolate US2209.

Like most vegetables varieties, spinach varieties are usually hybrids. The breeding of a hybrid spinach variety basically involves four steps: The first step comprises selecting and crossing of plants in order to obtain plants with desired traits, such as e.g. disease or pest resistances, better yield, better tolerance to climatic conditions, etc. The second step comprises selfing those plants with superior traits for several generations in order to produce inbred lines. Although these lines are different from each other, each line will become highly uniform after several generations of inbreeding. The third step comprises crossing the inbred lines to produce hybrid plants. Finally, the inbred lines that give rise to the best hybrid are identified. From there, commercial production of hybrid seed can start.

In one embodiment, the invention comprises a method of producing a hybrid spinach seed comprising crossing a first parent spinach plant with a second parent spinach plant and harvesting the resultant hybrid spinach seed, wherein said first parent spinach plant or said second parent spinach plant is a spinach plant of the invention, e.g., a spinach plant having resistance against downy mildew (*Peronospora farinose* f.sp. *spinaciae* (Pfs)) isolate US2209, or a spinach plant having resistance to downy mildew (*Peronospora farinose* f.sp. *spinaciae* (Pfs)) races 1, 3, 5, 8, 9, 11, or a spinach plant having resistance to both downy mildew (*Peronospora farinose* f.sp. *spinaciae* (Pfs)) isolate US2209, and downy mildew (*Peronospora farinose* f.sp. *spinaciae* (Pfs)) races 1, 3, 5, 8, 9, 11, or a spinach plant having any of the aforementioned resistance(s) and a combination of traits including medium bolting, fast growing, dark green leaf color at maturity, a round leaf tip, arrow shaped leafs, or a spinach plant having any of the aforementioned resistance(s) and one or more morphological or physiological characteristics tabulated herein, including a spinach plant of inbred spinach line SP6111, representative seed of which having been deposited under NCIMB 41758.

In another embodiment, the invention comprises producing a spinach plant being resistant against downy mildew (*Peronospora farinose* f.sp. *spinaciae* (Pfs)) isolate US2209 comprising: crossing a mother spinach plant with a father spinach plant to produce a hybrid seed; growing said hybrid seed to produce a hybrid plant; selfing said hybrid seed to produce F2 progeny seed; selecting said F2-plants for being resistant against downy mildew (*Peronospora farinose* f.sp. *spinaciae* (Pfs)) isolate US2209.

In still a further embodiment, the invention comprises a method of producing a spinach cultivar containing a combination of traits including medium bolting, fast growing, dark green leaf color at maturity, a round leaf tip, arrow shaped leafs, and resistance to downy mildew (*Peronospora farinose* f.sp. *spinaciae* (Pfs)) races 1, 3, 5, 8, 9, 11, and downy mildew isolate US2209 comprising: crossing a mother spinach plant with a father spinach plant to produce a hybrid seed; growing said hybrid seed to produce a hybrid plant; selfing said hybrid seed to produce F2 progeny seed; selecting said F2-plants for having medium bolting, fast growing, dark green leaf color at maturity, a round leaf tip, arrow shaped leafs, and resistance to downy mildew (*Peronospora farinose* f.sp. *spinaciae* (Pfs)) races 1, 3, 5, 8, 9, 11, and downy mildew isolate US2209.

The invention even further relates to a method of producing spinach comprising: (a) cultivating to the vegetative plant stage a plant of inbred spinach line SP6111, representative seed of which having been deposited under NCIMB Accession No. NCIMB 41758, and (b) harvesting spinach from the plant. The invention further comprehends canning, freezing or packaging the spinach plants or leaves.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, under deposit accession number NCIMB 41758 was made pursuant to the terms of the Budapest Treaty. Upon issuance of a patent, all restrictions upon the deposit will be removed, and the deposit is intended to meet the requirements of 37 CFR §1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following Detailed Description, including the Examples, given by way of example, but not intended to limit the invention solely to the specific embodiments described, may be best understood in conjunction with the accompanying drawings, incorporated herein by reference, in which:

FIGS. 1 and 2 are provided to assist the reader in appreciating the appearance round leaf tip, and arrow shaped leafs of the inventive spinach.

DETAILED DESCRIPTION OF THE INVENTION

Figure 1:
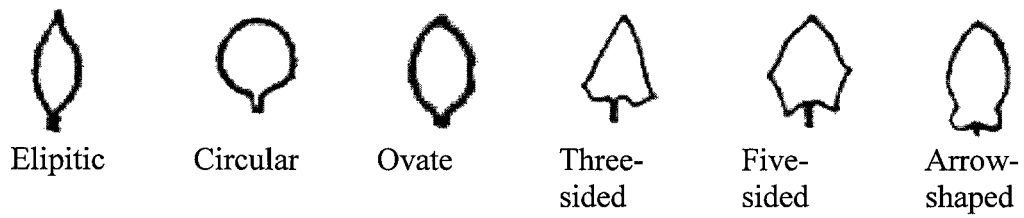
FIG. 1 shows leaf shapes.
Figure 2:
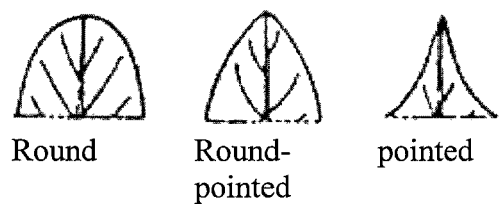
FIG. 2 shows leaf tip shapes.

The invention provides methods and compositions relating to plants, seeds and derivatives of a new inbred line of spinach plants herein referred to as inbred spinach line SP6111. Inbred spinach line SP6111 is a uniform and stable line, distinct from other such lines. Crossing inbred spinach line SP6111 with another distinct inbred spinach line will yield uniform F1 hybrid progeny plants.

The F1 may be self-pollinated to produce a segregating F2 generation. Individual plants may then be selected which represent the desired phenotype in each generation (F3, F4, F5, etc.) until the traits are homozygous or fixed within a breeding population. Inbred spinach line SP6111 was developed by half sib family selection out of GB25398. After 6 selection and selfing cycles. A final round of mass selection was performed, selecting for uniformity.

TABLE 1

Breeding history of SP6111 (M = mass selection).

| Year 1 | Pedigree selection from GB25398 |
| Year 1 | F2 Generation gown, no selection |
| Year 2 | F3 generation grown |
| Year 3 | F4 generation grown |
| Year 4 | F5 generation grown |
| Year 5 | F6 generation grown |
| Year 6 | F7 generation grown |
| Year 7 | F8 generation grown |
| Year 8 | F8.M1 |

In one embodiment, a plant of the invention has all the morphological and physiological characteristics of inbred spinach line SP6111. These physiological and morphological characteristics of spinach of the invention, e.g., line SP6111, are summarized in table 2. Embodiments of the invention advantageously have one or more, and most advantageously all, of these characteristics.

TABLE 2

Physiological and morphological characteristics of SP6111 and comparison variety Squirrel.

| Line/Cultivar<br>For patent or comparison | SP 6111<br>patent | Squirrel<br>Comparison |
|---|---|---|
| Characteristics | | |
| Species | *Spinacia oleracea* L. | *Spinacia oleracea* L. |
| Ploidy | Diploid | Diploid |
| Maturity | | |
| Growth Rate | Fast (Dixie Market) | Medium (Long Standing Bloomsdale) |
| Days from planting to prime market stage | 20 | 23 |
| Plant (prime market stage) | | |
| Habit | Semi-erect (long Standing Bloomsdale) | Flat (Viroflay) |
| Size | Small (America) | Large (Giant Nobel) |
| Spread (cm) | 33 | 50 |
| Height (cm) | 10 | 12 |
| Seedling Cotyledon | | |
| Width (mm) | 8 | 6 |
| Length (mm) | 65 | 45 |
| Tip | Rounded | |
| Color | Medium Green | Medium Green |
| Color Chart Name | RHS CC | — |
| Color Chart Value | 144 A | — |
| Leaf (First Foliage Leaves) | | |
| Shape | Ovate | Ovate |
| Base | Lobed | Lobed |
| Tip | Round | Round-pointed |
| Margin | Flat | Slightly Curled |
| Upper Surface Color | Dark Green (Long Standing Bloomsdale) | Dark Green (Long Standing Bloomsdale) |
| Color Chart Name | RHS CC | RHS CC |
| Color Chart Value | 137B | 137 A |
| Lower surface Color (compared with upper) | Lighter | Lighter |
| Color Chart Name | RHS CC | RHS CC |
| Color Chart Value | 137 C | 137 C |
| Leaf (Prime Market Stage) | | |
| Surface | Smooth (Viroflay) | Semi-savoy |
| Shape | Arrow-shaped | Arrow-shaped |
| Base | Lobed | Lobed |
| Tip | Round | Round |
| Margin | Flat | Slightly Curled |
| Upper Surface Color | Dark Green (Long Standing | Dark Green (Long Standing |

TABLE 2-continued

Physiological and morphological characteristics of SP6111 and comparison variety Squirrel.

| Line/Cultivar For patent or comparison | SP 6111 patent | Squirrel Comparison |
|---|---|---|
| | Bloomsdale) | Bloomsdale) |
| Color Chart Name | RHS CC | RHS CC |
| Color Chart Value | 137 B | 137 B |
| Lower surface Color (compared with upper) | Lighter | Lighter |
| Color Chart Name | RHS CC | RHS CC |
| Color Chart Value | 146 B | 146 B |
| Luster | Glossy | Dull |
| Blade Size | Medium (Virginia Savoy) | Large (Giant Nobel) |
| Blade Lobing | Lobed | Lobed |
| Petiole Color | Medium Green | Medium Green |
| Color Chart Name | RHS CC | RHS CC |
| Color Chart Value | 144 A | 144 C |
| Petiole Red Pigmentation | Absent | Absent |
| Petiole Length to the Blade (cm) | 5 | 5 |
| Petiole Length | Medium | Medium |
| Petiole Diameter (mm) | 5 | 5 |
| Petiole Diameter | Medium | Medium |
| Seed Stalk Development | | |
| Start of bolting (10% of the plants) | Medium (Long Standing Bloomsdale) | Medium (Long Standing Bloomsdale) |
| Height of Stalk (cm) | 60 | 60 |
| Leaves on Stalk of Female plant | Many | Many |
| Leaves on Stalk of Male plant | — | — |
| Plants that are Female | 91-100% | 91-100% |
| Plants that are Male | — | — |
| Plants that are Monoecious | | |
| Seed | | |
| Surface | Smooth | Smooth |
| Disease reaction | | |
| Pf1 | Resistant | Resistant |
| Pf2 | Susceptible | Resistant |
| P2 | Resistant | Resistant |
| Pf4 | Susceptible | Resistant |
| Pf5 | Resistant | Resistant |
| Pf6 | Susceptible | Resistant |
| Pf7 | Susceptible | Resistant |
| Pf8 | Resistant | Resistant |
| Pf9 | Resistant | Resistant |
| Pf10 | Susceptible | Resistant |
| Pf11 | Resistant | Resistant |
| Downy mildew isolate US2209 | Resistant | Susceptible |
| Fusarium | Susceptible | Not tested |
| White Rust | Not tested | Not tested |
| Curly Top Virus | Not tested | Not tested |
| CMV | Susceptible | Susceptible |
| Colletotrichum | Susceptible | Susceptible |
| Winter Hardiness | Not tested | Not tested |

In an embodiment, the invention relates to spinach plants that has all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into the plant of the invention, being a plant of inbred spinach line SP6111, by genetic transformation techniques; and, such plants of inbred spinach line SP6111 that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of inbred spinach line SP6111 or may, alternatively, be used for the preparation of transgenes which can be introduced by backcrossing. Methods for the transformation of plants, including spinach, are well known to those of skill in the art.

Vectors used for the transformation of spinach cells are not limited so long as the vector can express an inserted DNA in the cells. For example, vectors comprising promoters for constitutive gene expression in spinach cells (e.g., cauliflower mosaic virus 35S promoter) and promoters inducible by exogenous stimuli can be used. Examples of suitable vectors include pBI binary vector. The "spinach cell" into which the vector is to be introduced includes various forms of spinach cells, such as cultured cell suspensions, protoplasts, leaf sections, and callus. A vector can be introduced into spinach cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target spinach cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of inbred spinach line SP6111.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including spinach plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for spinach plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from spinach (psaD, psaF, psaE, PC, FNR, atpC, atpD, cab, rbcS) (see U.S. Pat. No. 7,161,061), the CAB-1 promoter from spinach (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the multileaf trait spinach of this invention include, for example, DNA sequences or genes from another species, or even genes or sequences which originate with or are present in spinach species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of inbred spinach line SP6111. Non-limiting examples of particular genes and corresponding phenotypes one may choose to introduce into a spinach plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof"

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed spinach and/or methods of transforming spinach or spinach plant cells, and techniques from these US patents, as well as promoters, vectors, etc., may be employed in the practice of this invention to introduce exogenous nucleic acid sequence(s) into a plant of inbred spinach line SP6111 (or cells thereof), and exemplify some exogenous nucleic acid sequence(s) which can be introduced into a plant of inbred spinach line SP6111 (or cells thereof) of the invention, as well as techniques, promoters, vectors etc., to thereby obtain further plants of inbred spinach line SP6111, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material comprises inter alia seeds of the claimed plant and parts of the plant that are suitable for sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems. (See generally U.S. Pat.

No. 7,041,876 on spinach being recognized as a plant that can be regenerated from cultured cells or tissue).

Also, the invention comprehends methods for producing a seed of a "SP6111"-derived spinach plant comprising (a) crossing a plant of inbred spinach line SP6111, representative seed of which having been deposited under NCIMB Accession No. NCIMB 41758, with a second spinach plant, and (b) whereby seed of a "SP6111"-derived spinach plant form (e.g., by allowing the plant from the cross to grow to producing seed). Such a method can further comprise (c) crossing a plant grown from "SP6111"-derived spinach seed with itself or with a second spinach plant to yield additional "SP6111"-derived spinach seed, (d) growing the additional "SP6111"-derived spinach seed of step (c) to yield additional "SP6111"-derived spinach plants, and (e) repeating the crossing and growing of steps (c) and (d) to generate further "SP6111"-derived spinach plants.

The invention additionally provides a method of introducing a desired trait into a plant of inbred spinach line SP6111 comprising: (a) crossing a plant of inbred spinach line SP6111, representative seed of which having been deposited under NCIMB Accession No. NCIMB 41758, with a second spinach plant that comprises a desired trait to produce F1 progeny; (b) selecting an F1 progeny that comprises the desired trait; (c) crossing the selected F1 progeny with a plant of inbred spinach line SP6111, to produce backcross progeny; (d) selecting backcross progeny comprising the desired trait and the physiological and morphological characteristic of a plant of inbred spinach line SP6111; and (e) repeating steps (c) and (d) three or more times in succession to produce selected fourth or higher backcross progeny that comprise the desired trait and all of the physiological and morphological characteristics of a plant of inbred spinach line SP6111, when grown in the same environmental conditions. The invention, of course, includes a spinach plant produced by this method.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of inbred spinach line SP6111, representative seed of which having been deposited under NCIMB Accession No. NCIMB 41758, is used in backcrossing, offspring retaining the combination of traits including medium bolting, fast growing, dark green leaf color at maturity, a round leaf tip, arrow shaped leafs, and resistance to downy mildew (*Peronospora farinose* f.sp. *spinaciae* (Pfs)) races 1, 3, 5, 8, 9, and 11 are progeny within the ambit of the invention. Backcrossing methods can be used with the present invention to improve or introduce a characteristic into a plant of the invention, being a plant of inbred spinach line 6111. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of inbred spinach line SP6111, representative seed of which has been deposited under NCIMB Accession No. NCIMB 41758, or a first generation progeny thereof, comprising obtaining a sample of nucleic acids from said plant and detecting in said nucleic acids a plurality of polymorphisms. This method can additionally comprise the step of storing the results of detecting the plurality of polymorphisms on a computer readable medium and/or transmitting the results of detecting the plurality of polymorphisms, e.g., by telephony or by means of computer (e.g., via email). The plurality of polymorphisms are indicative of and/or give rise to the expression of the morphological and physiological characteristics of inbred spinach line SP6111.

Spinach leaves are sold in packaged form, including without limitation as prepackaged spinach salad or as canned spinach or as frozen spinach. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach of the invention, as well as leaves of spinach derived from the invention. The invention further relates to a container comprising one or more plants of the invention, or one or spinach plants derived from a plant of the invention, in a growth substrate for harvest of leaves from the plant in a domestic environment. This way the consumer can pick very fresh leaves for use in salads. More generally, the invention includes one or more plants of the invention or one or more plants derived from spinach of the invention, wherein the plant is in a ready-to-harvest condition, including with the consumer picking his own, and further including a container comprising one or more of these plants.

Having thus described in detail preferred embodiments of the present invention, it is to be understood that the invention is not to be limited to particular details set forth in the above description as many apparent variations thereof are possible without departing from the spirit or scope of the present invention.

The invention claimed is:

1. A *Spinacia oleracea* ("spinach") plant designated SP6111, wherein the plant designated SP6111 exhibits a combination of traits including medium bolting, fast growing, dark green leaf color at maturity, a round leaf tip, arrow shaped leafs, and resistance to *Peronospora farinose* f.sp *spinaciae* (Pfs) races 1, 3, 5, 8, 9, 11, and to *Peronospora farinose* f.sp. *spinaciae* (Pfs) isolate US2209, representative seed of which having been deposited under NCIMB Accession No. 41758.

2. A seed of the plant of claim 1.

3. A part of the plant of claim 1, wherein said part is suitable for sexual reproduction.

4. The part of the plant as claimed in claim 3, wherein said part comprises a microspore, pollen, ovary, ovule, embryo sac or egg cell.

5. A part of the plant of claim 1, wherein said part is suitable for vegetative reproduction.

6. The part of the plant as claimed in claim 5, wherein said part comprises a cutting, root, stem, cell or protoplast.

7. A tissue culture of regenerable cells or protoplasts from the plant of claim 1.

8. The tissue culture as claimed in claim 7, wherein said cells or protoplasts of the tissue culture are derived from a tissue comprising a leaf, pollen, embryo, cotyledon, hypocotyl, meristematic cell, root, root tip, anther, flower, seed or stem.

9. An F1 progeny of the spinach plant of claim 1 ("the parent spinach plant"), wherein the progeny exhibits a combination of traits including medium bolting, fast growing, dark green leaf color at maturity, a round leaf tip, arrow shaped leafs, and resistance to *Peronospora farinose* f.sp *spinaciae* (Pfs) races 1, 3, 5, 8, 9, 11, and to *Peronospora farinose* f.sp. *spinaciae* (Pfs) isolate US2209, representative seed of which having been deposited under NCIMB Accession No. 41758.

10. The F1 progeny as claimed in claim 9, wherein said progeny is produced by sexual or vegetative reproduction of the parent spinach plant.

11. The F1 progeny of claim 9, wherein the progeny is further modified from the parent spinach plant in one or more other characteristics.

12. The F1 progeny as claimed in claim 11, wherein the modification is effected by mutagenesis.

13. The F1 progeny as claimed in claim 11, wherein the modification is effected by transformation with a transgene.

14. A method of producing a hybrid spinach seed comprising crossing a first parent spinach plant with a second parent spinach plant and harvesting the resultant hybrid spinach seed, wherein said first parent spinach plant or said second parent spinach plant is the spinach plant of claim 1.

15. A method of producing a *Spinacia oleracea* ("spinach") cultivar containing a combination of traits including medium bolting, fast growing, dark green leaf color at maturity, a round leaf tip, arrow shaped leafs, and resistance to *Peronospora farinose* f.sp. *spinaciae* (Pfs) races 1, 3, 5, 8, 9, 11, and *Peronospora farinose* f.sp. *spinaciae* (Pfs) isolate US2209 comprising: crossing a mother spinach plant with a father spinach plant to produce a hybrid seed, wherein the mother spinach plant or the father spinach plant is a spinach plant designated SP6111; growing said hybrid seed to produce a hybrid plant; selfing said hybrid plant to produce F2 progeny seed; growing said F2 progeny seed to produce F2-plants; selecting said F2-plants for having medium bolting, fast growing, dark green leaf color at maturity, round leaf tip, arrow shaped leafs, and resistance to *Peronospora farinose* f.sp. *spinaciae* (Pfs) races 1, 3, 5, 8, 9, 11, and *Peronospora farinose* f.sp. *spinaciae* (Pfs) isolate US2209, representative seed of which having been deposited under NCIMB Accession No. 41758.

16. A method for producing spinach leaves as a fresh vegetable comprising packaging leaves of a plant of claim 1.

17. A method for producing spinach leaves as a processed food comprising processing leaves of a plant of claim 1.

18. A container comprising or more spinach plants of claim 1 for harvest of leaves.

19. A *Spinacia oleracea* ("spinach") plant having all of the morphological and physiological characteristics of a spinach plant grown from seed deposited under NCIMB Accession No. 41758.

20. A method of introducing a desired trait into a plant of inbred spinach line SP6111 comprising:

(a) crossing a first spinach plant of inbred spinach line SP6111, representative seed of which having been deposited under NCIMB Accession No. 41758, with a second spinach plant that comprises the desired trait to produce F1 progeny;

(b) selecting an F1 progeny that comprises the desired trait;

(c) crossing the selected F1 progeny with a plant of inbred spinach line SP6111 to produce backcross progeny and (d) selecting backcross progeny comprising the desired trait and all of the physiological and morphological characteristics of a plant of inbred spinach line SP6111, when grown in the same environmental conditions.

21. The method of claim 20 further comprising (e) repeating steps (c) and (d) three or more times in succession to produce selected fourth or higher backcross progeny that comprise the desired trait and all of the physiological and morphological characteristics of a plant of inbred spinach line SP6111, when grown in the same environmental conditions.

22. A spinach plant produced by the method of claim 20 or 21.

23. A method for producing a seed of a SP6111-derived spinach plant comprising:

(a) crossing a first spinach plant of claim 1 or 19, with a second spinach plant, and (b) whereby seed of a SP6111-derived spinach plant forms.

24. The method of claim 23 further comprising:

(c) crossing a plant grown from SP6111-derived spinach seed with itself or with a second spinach plant to yield additional SP6111-derived spinach seed, (d) growing the additional SP6111-derived spinach seed of step (c) to yield additional SP6111-derived spinach plants, and (e) repeating the crossing and growing of steps (c) and (d) to generate further SP6111-derived spinach plants.

25. A method of determining the genotype of the plant of claim 1 or 19, or a first generation progeny thereof, comprising obtaining a sample of nucleic acids from said plant and detecting in said nucleic acids a plurality of polymorphisms, wherein the plurality of polymorphisms are indicative of and/or give rise to the expression of characteristics of the spinach plant or first generation progeny thereof.

26. The method of claim 25 additionally comprising the step of storing the results of detecting the plurality of polymorphisms on a computer readable medium, or transmitting the results of detecting the plurality of polymorphisms.

27. The spinach plant of claim 1, which is a plant grown from seed having been deposited under NCIMB Accession No. 41758.

28. A progeny of a spinach plant of claim 1, having all the morphological and physiological characteristics of the spinach plant of claim 7, representative seed of which having been deposited under NCIMB Accession No. 41758.

29. A hybrid spinach plant produced by the method of claim 14.

* * * * *